US011406755B1

(12) United States Patent
Schiff et al.

(10) Patent No.: US 11,406,755 B1
(45) Date of Patent: Aug. 9, 2022

(54) SENSING FLUID FLOW IRREGULARITIES IN AN ON-BODY INJECTOR

(71) Applicant: Fresenius Kabi Deutschland GmbH, Bad Homburg (DE)

(72) Inventors: David R. Schiff, Highland Park, NJ (US); Sharon D. West, Elkins Park, PA (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/180,221

(22) Filed: Feb. 19, 2021

(51) Int. Cl.
*A61M 5/142* (2006.01)
*A61M 5/145* (2006.01)
(Continued)

(52) U.S. Cl.
CPC ...... *A61M 5/14248* (2013.01); *A61M 5/1454* (2013.01); *A61M 2005/14208* (2013.01);
(Continued)

(58) Field of Classification Search
CPC .............. A61M 1/0025; A61M 1/0029; A61M 5/14244; A61M 5/14248; A61M 5/145; A61M 2005/14506; A61M 2005/14208; A61M 5/14252; A61M 5/1452; A61M 5/1454; A61M 5/16831; A61M 2005/16863; A61M 5/172;
(Continued)

(56) References Cited

U.S. PATENT DOCUMENTS

| 4,072,149 A | 2/1978 | Tischlinger |
| 4,234,104 A | 11/1980 | Apuzzo, Jr. et al. |

(Continued)

FOREIGN PATENT DOCUMENTS

| EP | 2242034 A1 | 10/2010 |
| WO | 2018081234 A1 | 5/2018 |

(Continued)

OTHER PUBLICATIONS

RightCare CGM Adhesive Universal Overpatches; Amazon available for sale May 6, 2020. https://www.amazon.com/Adhesive-Universal-Covered-Synthetic-Extreme/dp/B083QMYXQ7/ref=sr_1_27?keywords=overpatch&qid=163080153&sr=8-27&th=1 (Year: 2020).

(Continued)

*Primary Examiner* — Quynh-Nhu H. Vu
(74) *Attorney, Agent, or Firm* — Cook Alex Ltd.

(57) ABSTRACT

An on-body injector includes a drug reservoir with an associated temperature sensor. A piston having an associated force sensor is driven to convey a drug out of the drug reservoir during a drug delivery routine. The temperature and force sensors are electrically coupled to a controller that controls the components of the on-body injector to execute a drug delivery routine. The controller receives signals from the temperature sensor indicative of a temperature of the drug within the reservoir and from the force sensor indicative of a force experienced by the piston during the drug delivery routine. The controller analyzes the signals to determine whether the measured force is different from an expected force at the measured temperature. The controller generates an error signal when the measured force is different from the expected force at the measured temperature.

28 Claims, 3 Drawing Sheets

(51) Int. Cl.
*A61M 5/168* (2006.01)
*A61M 5/172* (2006.01)

(52) U.S. Cl.
CPC ............ *A61M 2005/14252* (2013.01); *A61M 2202/0007* (2013.01); *A61M 2205/18* (2013.01); *A61M 2205/332* (2013.01); *A61M 2205/3331* (2013.01); *A61M 2205/3368* (2013.01); *A61M 2205/3553* (2013.01); *A61M 2205/583* (2013.01)

(58) Field of Classification Search
CPC .... A61M 2205/332; A61M 2205/3331; A61M 2205/3368; A61M 2205/3375; A61M 2230/50; A61M 60/816
See application file for complete search history.

(56) References Cited

U.S. PATENT DOCUMENTS

| | | | |
|---|---|---|---|
| 4,970,502 | A | 11/1990 | Kunikane et al. |
| 6,620,134 | B1 | 9/2003 | Trombley, III et al. |
| 8,285,328 | B2 | 10/2012 | Caffey et al. |
| 9,452,255 | B2 | 9/2016 | Tieck et al. |
| 2002/0169439 | A1 | 11/2002 | Flaherty |
| 2003/0088238 | A1 | 5/2003 | Poulsen et al. |
| 2003/0167036 | A1 | 9/2003 | Flaherty |
| 2004/0068230 | A1 | 4/2004 | Estes et al. |
| 2004/0116866 | A1 | 6/2004 | Gorman et al. |
| 2004/0199123 | A1 | 10/2004 | Nielsen |
| 2006/0111671 | A1 | 5/2006 | Klippenstein |
| 2007/0290012 | A1 | 12/2007 | Jackman |
| 2008/0091139 | A1 | 4/2008 | Srinivasan et al. |
| 2008/0125700 | A1* | 5/2008 | Moberg ............ A61M 5/14244 604/67 |
| 2008/0269657 | A1 | 10/2008 | Brenneman et al. |
| 2009/0131860 | A1 | 5/2009 | Nielsen |
| 2010/0130931 | A1 | 5/2010 | Yodfat et al. |
| 2010/0262078 | A1* | 10/2010 | Blomquist .......... A61M 5/1452 604/151 |
| 2011/0060196 | A1 | 3/2011 | Stafford |
| 2011/0178461 | A1 | 7/2011 | Chong et al. |
| 2011/0196304 | A1 | 8/2011 | Kramer et al. |
| 2012/0010594 | A1 | 1/2012 | Holt et al. |
| 2013/0006213 | A1 | 1/2013 | Arnitz et al. |
| 2015/0374919 | A1 | 12/2015 | Gibson |
| 2016/0038689 | A1 | 2/2016 | Lee et al. |
| 2016/0082182 | A1 | 3/2016 | Gregory et al. |
| 2016/0175515 | A1 | 6/2016 | McCullough |
| 2016/0199574 | A1 | 7/2016 | Ring et al. |
| 2016/0220798 | A1 | 8/2016 | Netzel et al. |
| 2016/0296704 | A1 | 10/2016 | Gibson |
| 2016/0354555 | A1 | 12/2016 | Gibson et al. |
| 2016/0374707 | A1 | 12/2016 | Akagane |
| 2017/0119969 | A1 | 5/2017 | McCullough et al. |
| 2017/0124284 | A1 | 5/2017 | McCullough et al. |
| 2017/0147787 | A1 | 5/2017 | Albrecht et al. |
| 2017/0182253 | A1 | 6/2017 | Folk et al. |
| 2017/0312454 | A1 | 11/2017 | Chattaraj et al. |
| 2017/0340837 | A1 | 11/2017 | Nazzaro et al. |
| 2017/0361015 | A1 | 12/2017 | McCullough |
| 2017/0368260 | A1 | 12/2017 | McCullough et al. |
| 2018/0021508 | A1 | 1/2018 | Destefano et al. |
| 2018/0028747 | A1 | 2/2018 | Hanson et al. |
| 2018/0036476 | A1 | 2/2018 | McCullough et al. |
| 2018/0085517 | A1 | 3/2018 | Laurence et al. |
| 2018/0193557 | A1 | 7/2018 | Johnson et al. |
| 2018/0256823 | A1 | 9/2018 | Nazzaro et al. |
| 2018/0272059 | A1 | 9/2018 | Marbet et al. |
| 2018/0304014 | A1 | 10/2018 | Knudsen et al. |
| 2019/0009019 | A1* | 1/2019 | Shor .................. A61M 5/1723 |
| 2019/0022306 | A1 | 1/2019 | Gibson et al. |
| 2019/0050375 | A1 | 2/2019 | Fitzgibbon et al. |
| 2019/0060562 | A1 | 2/2019 | Olivas et al. |
| 2019/0083702 | A1 | 3/2019 | Nekouzadeh et al. |
| 2019/0134296 | A1 | 5/2019 | Barbedette et al. |
| 2019/0143043 | A1 | 5/2019 | Coles et al. |
| 2019/0143047 | A1 | 5/2019 | Jazayeri et al. |
| 2019/0151544 | A1 | 5/2019 | Stonecipher |
| 2019/0167899 | A1 | 6/2019 | Cabiri |
| 2019/0167908 | A1 | 6/2019 | Fitzgibbon et al. |
| 2019/0192766 | A1 | 6/2019 | Stonecipher |
| 2019/0247579 | A1 | 8/2019 | Damestani et al. |
| 2019/0275241 | A1 | 9/2019 | Ring et al. |
| 2019/0328965 | A1 | 10/2019 | Moberg |
| 2019/0365986 | A1 | 12/2019 | Coiner et al. |
| 2019/0374707 | A1 | 12/2019 | Damestani et al. |
| 2019/0381238 | A1 | 12/2019 | Stonecipher et al. |
| 2020/0023122 | A1 | 1/2020 | McCullough et al. |
| 2020/0164145 | A1 | 5/2020 | Chang et al. |
| 2020/0164155 | A1 | 5/2020 | Mojarrad et al. |
| 2020/0179609 | A1 | 6/2020 | Tan-Malecki et al. |
| 2020/0197628 | A1 | 6/2020 | McCullough et al. |
| 2020/0206429 | A1 | 7/2020 | Hering et al. |
| 2020/0230313 | A1 | 7/2020 | Mojarrad et al. |
| 2020/0238004 | A1 | 7/2020 | McCullough |
| 2020/0254172 | A1 | 8/2020 | Forster et al. |
| 2020/0254185 | A1 | 8/2020 | Bar-El et al. |
| 2020/0261643 | A1 | 8/2020 | Boyaval et al. |
| 2020/0261648 | A1 | 8/2020 | Groszmann et al. |
| 2020/0261657 | A1 | 8/2020 | Gibson et al. |
| 2020/0289745 | A1 | 9/2020 | Harris et al. |
| 2020/0297927 | A1 | 9/2020 | Conrath et al. |
| 2020/0315918 | A1 | 10/2020 | Naygauz |
| 2020/0322793 | A1 | 10/2020 | Yang |
| 2020/0338271 | A1 | 10/2020 | Harris et al. |
| 2021/0228799 | A1 | 7/2021 | Streit et al. |

FOREIGN PATENT DOCUMENTS

| | | |
|---|---|---|
| WO | 2018183039 A1 | 10/2018 |
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

OTHER PUBLICATIONS

Omnipod Grip Shield Designed by Deck My Diabetes; Amazon. Available for sale Dec. 14, 2020 https://www.amazon.com/Deck-My-Diabetes-Flexible-Additional/dp/B08QL3TVZB/ref=sr_1_6?keywords=insulin+pump+overlay&qid=1639074568&sr=8-6 (Year: 2020).

* cited by examiner

SENSING FLUID FLOW IRREGULARITIES IN AN ON-BODY INJECTOR

BACKGROUND

Field of the Disclosure

The present disclosure relates to drug delivery devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or alight emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, if fluid flow becomes blocked or otherwise reduced with respect to an expected fluid flow profile, the patient may not receive the proper amount of the drug at the proper time. Thus, it would be advantageous for a device to be able to diagnose a possible occlusion or irregularity in drug delivery and alert the patient or a health care professional.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an on-body injector includes a housing and an adhesive pad associated with a lower surface of the housing and configured to be removably attached to a human body surface. A drug reservoir is positioned within the housing, with a temperature sensor associated with the drug reservoir and a needle fluidly connected to the drug reservoir. A piston includes a piston head movably positioned within the drug reservoir to convey a drug out of the drug reservoir during a drug delivery routine. The piston also includes a piston rod associated with the piston head and extending outside of the drug reservoir and a force sensor. A controller is electrically coupled to the temperature sensor and the force sensor and configured to control the components of the on-body injector to execute a drug delivery routine. The controller is further configured to receive signals from the temperature sensor indicative of a temperature of the drug within the drug reservoir and from the force sensor indicative of a force experienced by the piston during said drug delivery routine. The controller analyzes the signals from the sensors to determine whether the measured force is different from an expected force at the measured temperature. If so, the controller generates an error signal.

In another aspect, a method is provided of monitoring fluid flow through an on-body injector. The method includes beginning a drug delivery routine in which a piston head of a piston is moved within a drug reservoir to convey a drug from the drug reservoir to a patient. A temperature that is indicative of a temperature of the drug in the drug reservoir is measured during the drug delivery routine, with a force indicative of a force experienced by the piston during the drug delivery routine also being measured. It is then determined whether the measured force is different from an expected force at the measured temperature. An error signal is generated when the measured force is different from the expected force at the measured temperature.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
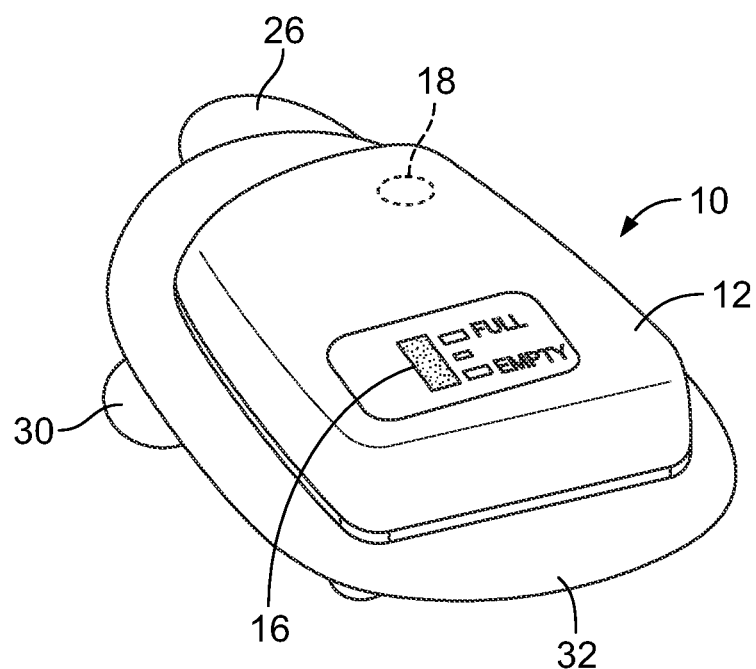
FIG. 1 is a top perspective view of a drug delivery device according to conventional design.
Figure 2:
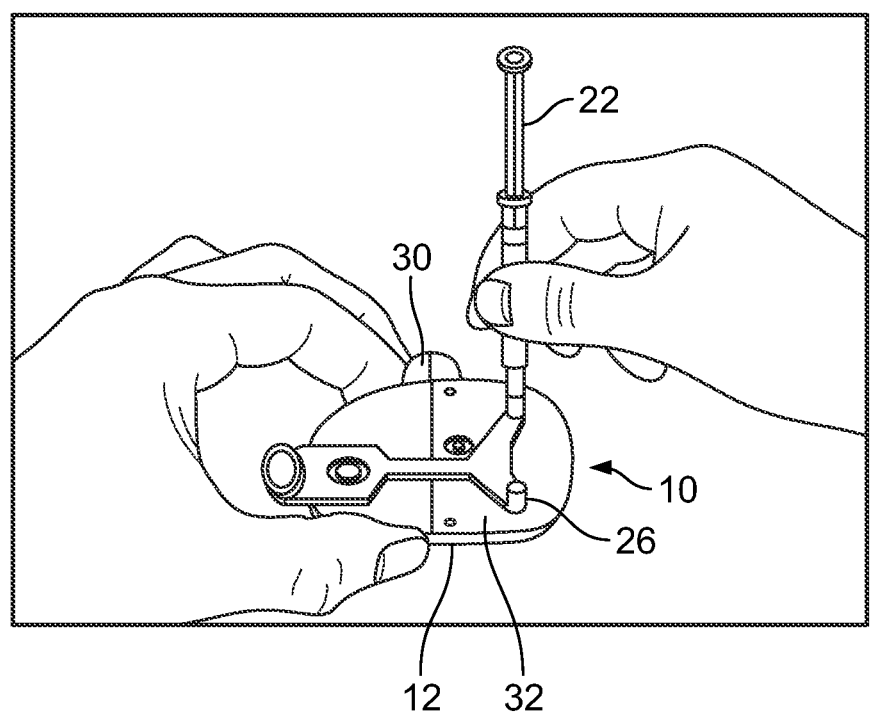
FIG. 2 is a bottom perspective view of the drug delivery device of FIG. 1.
Figure 3:
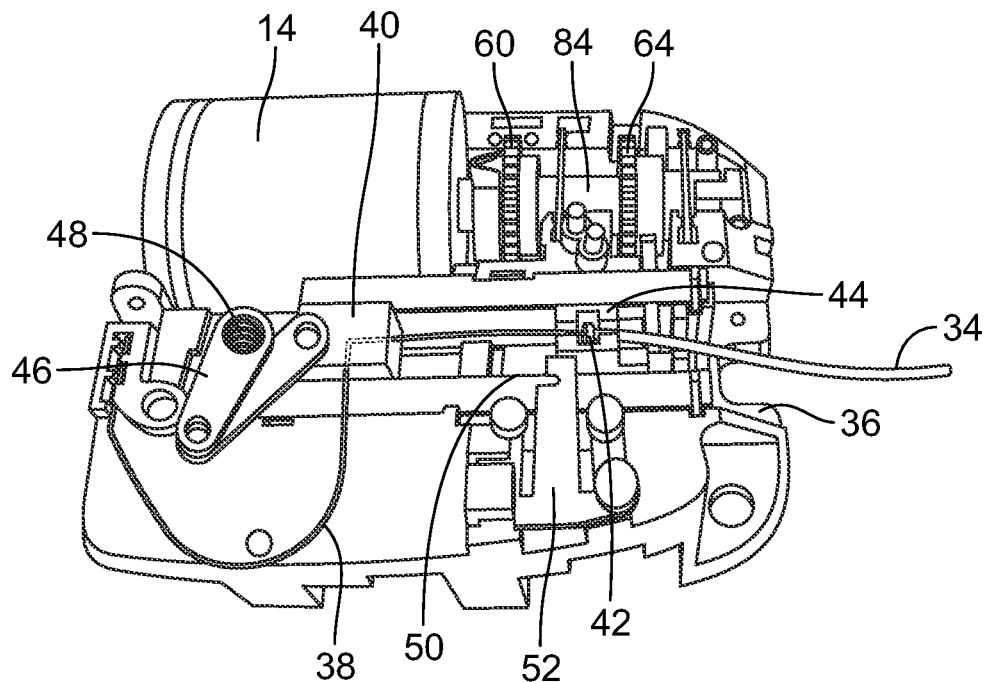
FIG. 3 is a top perspective view of the interior components of the drug delivery device of FIG. 1.
Figure 4:
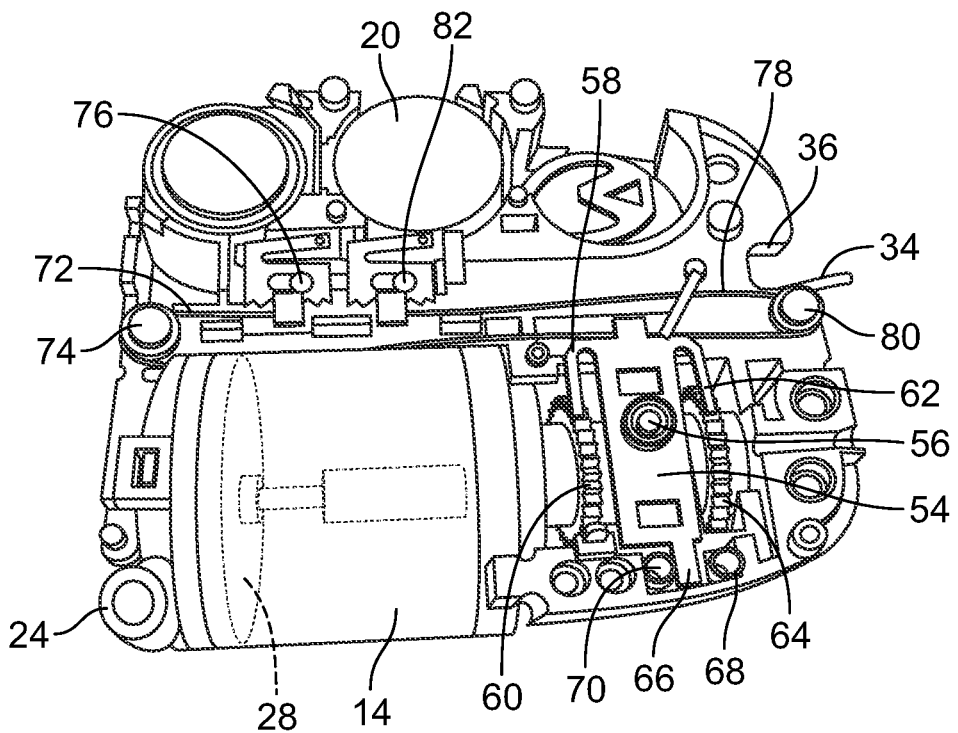
FIG. 4 is a bottom perspective view of the interior components of the drug delivery device of FIG. 1.
Figure 5:
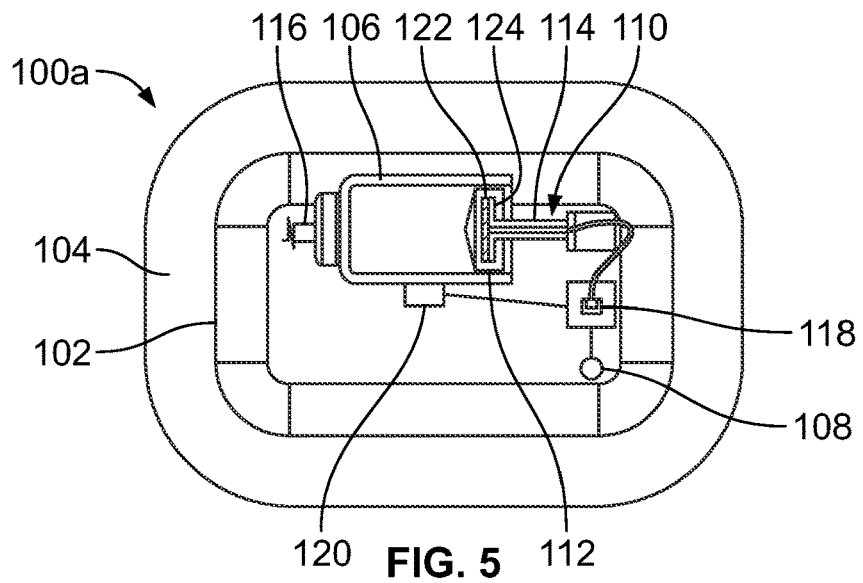
FIG. 5 is a top plan view of selected components of an exemplary embodiment of a drug delivery device according to an aspect of the present disclosure.
Figure 6:
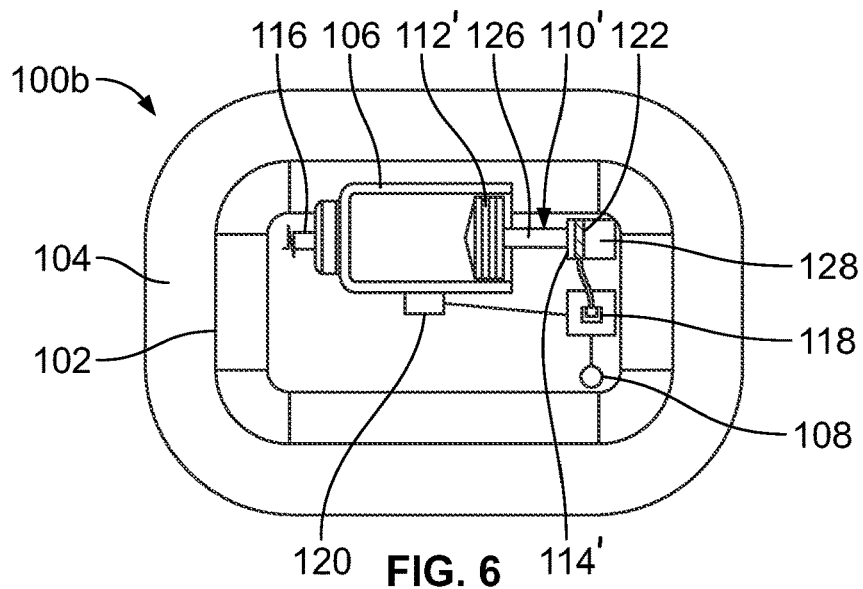
FIG. 6 is a top plan view of selected components of another exemplary embodiment of a drug delivery device according to an aspect of the present disclosure.
Figure 7:
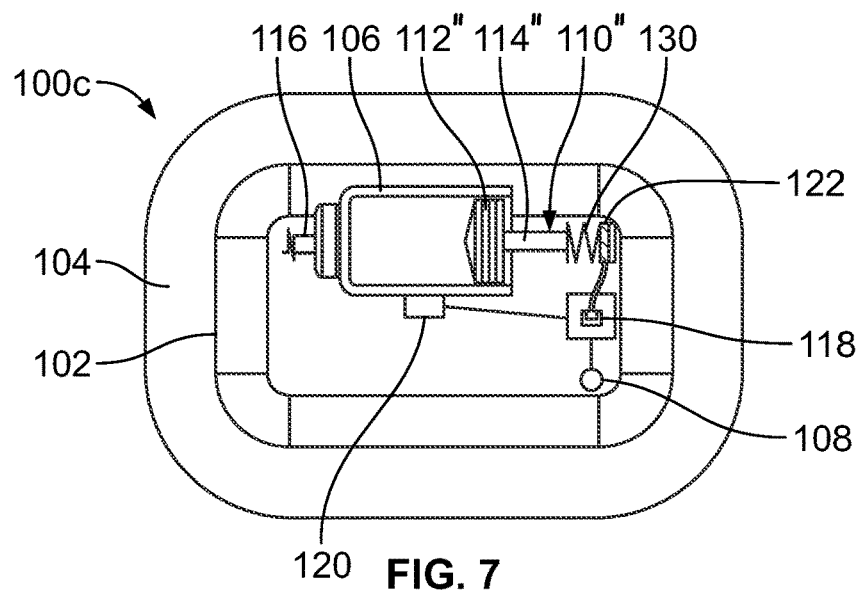
FIG. 7 is a top plan view of selected components of yet another exemplary embodiment of a drug delivery device according to an aspect of the present disclosure.

FIGS. 5-7 illustrate on-body injectors 100a, 100b, and 100c embodying aspects of the present disclosure, whereby the temperature of the drug in a drug reservoir and the force experienced by a piston during a drug delivery routine are used to determine whether fluid flow through an on-body injector is prevented, reduced, or otherwise irregular. The on-body injectors 100a, 100b, and 100c of FIGS. 5-7 are not illustrated in detail, but rather only selected components are shown and described herein. It should be understood that the components not shown and/or described in detail herein may be provided according to any suitable configuration, which includes the components being configured and functioning as described above with regard to the conventional device 10 of FIGS. 1-4.

In the embodiment of FIG. 5, the on-body injector 100a includes a housing 102 that contains or encloses the functional components of the on-body injector 100a. An adhesive pad 104 is associated with a lower surface of the housing 102 for removably attaching the on-body injector 100a to a human body surface (e.g., to an arm or an abdomen). A release film may be associated with the adhesive pad 104 and removed just prior to securing the adhesive pad 104 to the body of a patient, as described above with regard to the conventional device 10 of FIGS. 1-4.

A drug reservoir 106 (which may be configured generally according to the above description of the reservoir 14 of the device 10 of FIGS. 1-4) is contained within the housing 102. The drug reservoir 106 is configured to contain a liquid drug, which may be injected therein via a port (as described with regard to the device 10 of FIGS. 1-4) or may be provided therein by any suitable approach without departing from the scope of the present disclosure. An upper surface of the housing 102 may include a fill indicator that provides a visual indication of the amount of fluid in the drug reservoir 106. The upper surface of the housing 102 may also be configured to allow a status light 108 (which may be configured as a light-emitting diode) mounted within the housing 102 to be seen, though it is also within the scope of the present disclosure for the status light 108 (if provided) to be visible through some other surface of the housing 102.

A piston 110 includes a piston head 112 positioned within the drug reservoir 106, with a piston rod 114 associated with the piston head 112 extending outside of the drug reservoir 106. The piston head 112 and piston rod 114 may be variously configured without departing from the scope of the present disclosure, with the piston head 112 being at least partially formed of an elastomeric material (e.g., a rubber material) and the piston rod 114 formed of a generally rigid material (e.g., a plastic material or a metallic material) in an exemplary embodiment.

Regardless of the particular configuration of the piston 110, it is configured to move with respect to the drug reservoir 106 (with the piston head 112 moving through the interior of the drug reservoir 106) to convey a drug out of the drug reservoir 106. The mechanism by which the piston 110 is moved with respect to the drug reservoir 106 may vary without departing from the scope of the present disclosure, with the piston 110 being moved by a muscle wire and lever assembly of the type described above with regard to the device 10 of FIG. 1-4 in an exemplary embodiment.

In the orientation of FIG. 5, the piston 110 is moved from right to left to convey the drug out of the drug reservoir 106 via a needle 116 fluidly connected to the drug reservoir 106. While FIG. 5 shows the needle 116 directly connected to the drug reservoir 106, it should be understood that there may be one or more intermediary components (e.g., a tube) interposed between an outlet port of the drug reservoir 106 and the needle 116 to facilitate fluid flow from the drug reservoir 106 to the needle 116. As described above with regard to the device 10 of FIGS. 1-4, a distal end of the needle 116 may be sharpened or beveled for piercing the skin of a patient for drug delivery. As also described above, a flexible cannula may be associated with the needle 116, with the needle 116 piercing the skin and then being withdrawn, while the distal end of the flexible cannula remains within the skin for drug delivery to the patient.

The status light 108 (and the other electrical components of the on-body injector 100a) is electrically coupled to a controller or processor 118 (which may be a CPU or MPU configured as a computer chip mounted to a printed circuit board positioned within the housing 102, for example) that carries software for executing a drug delivery routine. The exact steps carried out by the various electrical components of the on-body injector 100a may vary without departing from the scope of the present disclosure, but will include the controller 118 instructing or actuating a motor or similar drive mechanism (e.g., the above-described muscle wire and lever assembly) to cause the piston 110 to move with respect to the drug reservoir 106 (in a right to left direction in the orientation of FIG. 5) to convey the drug out of the drug reservoir 106, through the needle 116, and into the body of a patient.

The controller 118 is configured to execute the drug delivery routine to deliver a predetermined amount of drug to a patient at a predetermined time and according to a predetermined fluid flow profile. Thus, if fluid flow becomes blocked or otherwise reduced with respect to an expected fluid flow profile, the patient may not receive the proper amount of the drug at the proper time. Blocked or reduced fluid flow will lead to an increase in the pressure within the drug reservoir 106, as the piston 110 must exert more force to move the drug out of the drug reservoir 106. An increase in pressure will also lead to an increase in temperature of the drug in the drug reservoir 106, though such a temperature increase will typically be nominal, with an increase in force generally being more prominent and indicative of a flow irregularity. The force required to move the drug out of the drug reservoir 106 is dependent upon the temperature of the drug, with warmer fluid tending to flow more freely than cooler fluid. Accordingly, to detect an irregularity in fluid flow through the on-body injector 100a, a temperature sensor 120 associated with the drug reservoir 106 and a force sensor 122 associated with the piston 110 are electrically coupled to the controller 118. The temperature sensor 120 measures a temperature of a portion of the drug reservoir 106 and/or the drug contained within the drug reservoir 106 and transmits that information to the controller 118, while the force sensor 122 measures a force experienced by the piston 110 during a drug delivery routine and transmits that information to the controller 118.

The controller 118 is programmed with a force-temperature relationship, which it compares to the measured temperature and the measured force. When the measured force differs from the force that is expected to be required to dispense a certain drug at the measured temperature, it is indicative of there being some irregularity in the flow of fluid through the on-body injector 100a. Upon determining that there is some irregularity in fluid flow, the controller 118 generates an error signal to alert the patient and/or a health care professional. This may include, for example, the error signal being transmitted to the status light 108 to cause the status light 108 to provide a visual indication of an error (e.g., by presenting a different color light and/or changing a pattern in which the status light 108 blinks). This may also or alternatively include, for example, the error signal being wirelessly transmitted to a separate electronic device, such as a smartphone or computer or the like, to alert a health care professional. The controller 118 may take additional actions (e.g., ending or pausing the drug delivery routine or attempting to correct fluid flow by adjusting the operation of one or more components of the on-body injector 100a) without departing from the scope of the present disclosure.

On-body injectors according to the present disclosure may be used in combination with a wide variety of liquid drugs or drug solutions, with there being different force-temperature relationships for different drugs. For example, in one embodiment, the methods and devices described herein are used to deliver pegfilgrastim to a subject. Other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin. On account of the wide variety of drugs that may be dispensed, the controller 118 may be programmed with a force-temperature relationship that is customized to the drug to be dispensed.

The expected force required to dispense a drug at a given temperature may depend not only on the nature of the drug being dispensed, but also on the particular configuration of the on-body injector. Accordingly, that it may be advantageous for the force-temperature relationship programmed into the controller 118 to be experimentally determined. For example, a drug to be dispensed may be brought to a particular temperature in a laboratory setting. The drug (at the known temperature) is dispensed using the on-body injector, with the temperature sensor 120 ensuring that the drug remains at the selected temperature and the force sensor 122 measuring the force required to dispense the drug at that temperature. This process is repeated several times for the same drug at different temperatures, with each measured force being recorded as the expected force to dispense the drug at the corresponding measured temperature. With this experimental data, the force-temperature relationship for that particular drug and device combination may be calculated or derived and programmed into the controller 118. It should be understood that this process need not be repeated for every unit of an on-body injector, but rather may be done just once and applied to all identically configured devices to be used to dispense the same drug.

While an increase in the force experienced by the piston 110 during a drug delivery routine may, on its own, be indicative of a blockage or reduction in fluid flow, considering the temperature of the drug in the drug reservoir 106 (which effects the force required to dispense the drug) will better ensure that the controller 118 does not improperly diagnose an irregularity in fluid flow. For example, a small increase in force may not indicate when the drug is relatively cold, but may indicate a blockage or irregularity when the drug is warmer. Thus, by considering the temperature of the drug when analyzing an increase in the force experienced by the piston 110 during drug delivery, the controller 118 will be able to more accurately identify a flow irregularity than if only force were considered in assessing fluid flow.

The exact configuration of the temperature sensor 120 and the force sensor 122 may vary without departing from the scope of the present disclosure. For example, in the embodiment of FIG. 5, the temperature sensor 120 is configured as a thermistor at least partially secured to a surface of the drug reservoir 106. As explained above, the temperature of the drug in the drug reservoir 106 is relevant to the determination of whether there is a flow irregularity or interruption (with an elevated temperature being indicative of a possible irregularity), so it may be advantageous for at least a portion of the temperature sensor 120 to communicate with the interior of the drug reservoir 106 to directly monitor the temperature of the drug. Alternatively, if the drug reservoir 106 (or at least a portion thereof) is configured to transmit or conduct heat (rather than being insulated), it may be sufficient for the temperature sensor 120 to be secured to and monitor the temperature of an outer surface of the drug reservoir 106, as that temperature will be indicative of the temperature of the drug contained within the drug reservoir 106.

As for the force sensor 122, it is shown in FIG. 5 as being at least partially positioned within the piston head 112. In this embodiment, the piston rod 114 is not fixedly secured to the piston head 112, but rather an end of the piston rod 114 is secured or associated with the force sensor 122, which is at least partially received within a cavity 124 defined by the piston head 112. The force sensor 122 is movable back-and-forth within the cavity 124, such that the force sensor 122 will be pressed between the associated end of the piston rod 114 and an opposing surface of the piston head 112 when the piston 110 is driven to convey the drug out of the drug reservoir 106 (with the drug exerting a force that opposes movement of the piston head 112 through the drug reservoir 106). In such an embodiment, the force sensor 122 may be configured as a pressure sensor (e.g., a piezoelectric pressure sensor), though it is within the scope of the present disclosure for the force sensor 122 to be differently configured. The amount of resistance that the drug provides to oppose the movement of the piston head 112 is indicative of the nature of fluid flow from the drug reservoir 106 to the patient, with an elevated resistance (translating to increased force experienced by the piston 110 and a greater pressure reading transmitted from the force sensor 122 to the controller 118) being indicative of a possible occlusion or other flow irregularity.

FIG. 6 illustrates an on-body injector 100b that is similarly configured to the on-body injector 100a of FIG. 5, but employs a differently configured piston 110'. In the embodiment of FIG. 6, the piston 110' is comprised of a piston head 112' fixedly secured to a first portion 126 of a piston rod 114'. The piston rod 114' includes a second portion 128, with a force sensor 122 at least partially positioned between the two portions 126 and 128 of the piston rod 114'. The force applied to drive and move the piston 110' is applied to the second portion 128 of the piston rod 114', such that the second portion 128 will press against the force sensor 122, which will press against the first portion 126 of the piston rod 114' to move the piston head 112' through the drug reservoir 106. By such a configuration, the force sensor 122 will be pressed between the two portions 126 and 128 of the piston rod 114' when the piston 110' is driven to convey the drug out of the drug reservoir 106 (with the drug exerting a force that opposes movement of the piston head 112' through the drug reservoir 106). As in the embodiment of FIG. 5, the force sensor 122 may be configured as a pressure sensor (e.g., a piezoelectric pressure sensor), though the force sensor 122 may be differently configured without departing from the scope of the present disclosure. As described above with regard to the embodiment of FIG. 5, the amount of resistance that the drug provides to oppose the movement of the piston head 112' is indicative of the nature of fluid flow from the drug reservoir 106 to the patient, with an elevated resistance (translating to increased force experienced by the piston 110' and a greater pressure reading transmitted from the force sensor 122 to the controller 118) being indicative of a possible occlusion or other flow irregularity.

FIG. 7 illustrates another on-body injector 100c that is similarly configured to the on-body injector 100a of FIG. 5 and the on-body injector 100b of FIG. 6, but employs a differently configured piston 110". In the embodiment of FIG. 7, the piston 100" is comprised of a piston head 112" fixedly secured to a piston rod 114". A spring 130 is associated with the piston rod 114" and/or the piston head 112", with the piston 110" being configured such that movement of the piston 110" to convey the drug out of the drug reservoir 106 will cause deformation of the spring 130. A force sensor 122 (which may be configured as a strain gauge in this embodiment) is associated with the spring 130, with the force sensor 122 transmitting signals to the controller 118 that are indicative of any deformation of the spring 130, which deformation is indicative of the force experienced by the piston 110" during a drug delivery routine. As described above with regard to the embodiment of FIG. 5, the amount of resistance that the drug provides to oppose the movement of the piston head 112" is indicative of the nature of fluid flow from the drug reservoir 106 to the patient, with an elevated resistance (translating to increased force experienced by the piston 110", increased deformation of the spring 130, and a greater strain reading transmitted from the force sensor 122 to the controller 118) being indicative of a possible occlusion or other flow irregularity.

In addition to the basic force-temperature relationship, the controller 118 may be programmed with further protocols. For example, in one embodiment, rather than any difference from the expected force being treated as indicative of a fluid flow irregularity, the controller 118 may instead be configured to assess the magnitude of a difference between a measured and an expected value. For example, the controller 118 may be configured to only generate an error signal if the measured force is a minimum percentage (e.g., 10%) above the expected value. This may be advantageous to prevent an error signal from being prematurely or unnecessarily generated (e.g., an error signal may be inappropriate if the measured force momentarily increases above the expected level before returning to the expected level).

Another approach to preventing premature or unnecessarily generated error signals includes configuring the controller 118 to require a certain number of consecutive readings that are elevated or readings that are elevated for a particular amount of time. Yet another approach includes configuring the controller 118 to only generate an error signal after attempts to remedy a fluid flow irregularity have proven unsuccessful. Such configurations better ensure that the on-body injector 100a, 100b, 100c is experiencing a fluid flow irregularity that is not transitory or that is irreversible, such that the most appropriate action is to generate an error signal (and optionally pause or end the drug delivery routine).

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:
1. An on-body injector comprising:
a housing;

an adhesive pad associated with a lower surface of the housing and configured to be removably attached to a human body surface;
a drug reservoir positioned within the housing;
a temperature sensor associated with the drug reservoir;
a needle fluidically connected to the drug reservoir;
a piston including
   a piston head movably positioned within the drug reservoir to convey a drug out of the drug reservoir during a drug delivery routine,
   a piston rod associated with the piston head and extending outside of the drug reservoir, and
   a force sensor; and
a controller electrically coupled to the temperature sensor and the force sensor and configured to execute said drug delivery routine, wherein the controller is configured to
   receive signals from the temperature sensor indicative of a temperature of the drug within the drug reservoir and from the force sensor indicative of a force experienced by the piston during said drug delivery routine,
   analyze the signals from the temperature sensor and the force sensor to determine whether a measured force is different from an expected force at a measured temperature, and
   generate an error signal when the measured force is different from the expected force at the measured temperature.

2. The on-body injector of claim 1, wherein the force sensor is at least partially positioned within the piston head.

3. The on-body injector of claim 1, wherein the force sensor is at least partially positioned between separate first and second portions of the piston rod.

4. The on-body injector of claim 1, wherein the force sensor is associated to the piston by a spring.

5. The on-body injector of claim 1, wherein the force sensor comprises a pressure sensor.

6. The on-body injector of claim 1, wherein the force sensor comprises a piezoelectric pressure sensor.

7. The on-body injector of claim 1, wherein the force sensor comprises a strain gauge.

8. The on-body injector of claim 1, wherein the temperature sensor comprises a thermistor.

9. The on-body injector of claim 1, further comprising a status light electrically coupled to the controller, wherein the error signal generated by the controller is transmitted to the status light.

10. The on-body injector of claim 1, wherein the error signal generated by the controller is wirelessly transmitted to a separate electronic device.

11. The on-body injector of claim 1, wherein the controller is programmed with a force-temperature relationship for pegfilgrastim.

12. A method of monitoring fluid flow through an on-body injector comprising a housing, an adhesive pad associated with a lower surface of the housing and configured to be removably attached to a human body surface, a drug reservoir positioned within the housing, a needle fluidically connected to the drug reservoir, a piston including a piston head movably positioned within the drug reservoir and a piston rod associated with the piston head and extending outside of the drug reservoir, the method comprising:
   beginning a drug delivery routine in which the piston head is moved within the drug reservoir to convey a drug from the drug reservoir to a patient;
   measuring a temperature indicative of a temperature of the drug in the drug reservoir during the drug delivery routine;
   measuring a force indicative of a force experienced by the piston during the drug delivery routine;
   determining whether the measured force is different from an expected force at the measured temperature; and
   generating an error signal when the measured force is different from the expected force at the measured temperature.

13. The method of claim 12, wherein the force is measured at a position within the piston head.

14. The method of claim 12, wherein the force is measured at a position between separate first and second portions of the piston rod.

15. The method of claim 12, wherein the force is measured at a position associated to the piston by a spring.

16. The method of claim 12, wherein the force is measured by a pressure sensor.

17. The method of claim 12, wherein the force is measured by a piezoelectric pressure sensor.

18. The method of claim 12, wherein the force is measured by a strain gauge.

19. The method of claim 12, wherein the temperature is measured by a thermistor.

20. The method of claim 12, wherein the error signal is transmitted to a status light of the drug delivery device.

21. The method of claim 12, wherein the error signal is wirelessly transmitted to a separate electronic device.

22. The method of claim 12, wherein the drug comprises pegfilgrastim.

23. A fluid flow monitoring system for an on-body injector of the type comprising a housing configured to be removably associated to a human body surface, a drug reservoir positioned within the housing, and a needle fluidically connected to the drug reservoir, the fluid flow monitoring system comprising:
   a temperature sensor;
   a force sensor; and
   a controller electrically coupled to the temperature sensor and the force sensor, wherein the controller is configured to receive signals from the temperature sensor and from the force sensor and analyze the signals from the temperature sensor and the force sensor to determine whether a measured force is different from an expected force at a measured temperature.

24. The fluid flow monitoring system of claim 23, wherein
   the controller is configured to execute a drug delivery routine,
   the signals from the temperature sensor are indicative of a temperature of a drug within a drug reservoir of an on-body injector,
   the signals from the force sensor are indicative of a force experienced in conveying the drug from the drug reservoir during said drug delivery routine, and
   the controller is configured to determine that there is a fluid flow irregularity when the measured force is different from the expected force at the measured temperature.

25. The on-body drug injector of claim 1, wherein the controller is configured to communicate wirelessly with a separate electronic device.

26. The method of claim 12, further comprising communicating wirelessly with a separate electronic device.

27. The fluid flow monitoring system of claim 23, wherein the controller is configured to communicate wirelessly with a separate electronic device.

28. An on-body injector comprising:
a housing;
a drug reservoir positioned within the housing;
a controller configured to control the components of the on-body injector to execute a drug delivery routine in which a drug is conveyed out of the drug reservoir;
a temperature sensor electrically coupled to the controller; and
a force sensor electrically coupled to the controller, wherein the controller is configured to
   receive signals from the temperature sensor and from the force sensor during said drug delivery routine, and
   analyze the signals from the temperature sensor and the force sensor to determine whether a measured force is different from an expected force at a measured temperature.

\* \* \* \* \*